(12) United States Patent
Kwetkat et al.

(10) Patent No.: US 6,710,022 B1
(45) Date of Patent: Mar. 23, 2004

(54) TENSIDE COMPOSITION CONTAINING GEMINI TENSIDES AND CO-AMPHIPHILES AND PRODUCTION AND USE THEREOF

(75) Inventors: Klaus Kwetkat, Bergkamen (DE); Gerd H. Dahms, Duisburg (DE)

(73) Assignee: Sasol Germany GmbH (DE)

( * ) Notice: Subject to any disclaimer, the term of this patent is extended or adjusted under 35 U.S.C. 154(b) by 0 days.

(21) Appl. No.: 09/831,796

(22) PCT Filed: Sep. 13, 2000

(86) PCT No.: PCT/DE00/03162
§ 371 (c)(1),
(2), (4) Date: Aug. 14, 2001

(87) PCT Pub. No.: WO01/19945
PCT Pub. Date: Mar. 22, 2001

(30) Foreign Application Priority Data

Sep. 13, 1999 (DE) .......................................... 199 43 668

(51) Int. Cl.⁷ ............................. C11D 1/00; C11D 3/26; C11D 3/30; C11D 3/43; C11D 3/44
(52) U.S. Cl. ........................ 510/119; 510/130; 510/137; 510/138; 510/158; 510/159; 510/499; 510/506; 510/488
(58) Field of Search .................................. 510/119, 130, 510/137, 138, 158, 159, 499, 506, 488

(56) References Cited

U.S. PATENT DOCUMENTS

| | | | | |
|---|---|---|---|---|
| 5,789,371 A | * | 8/1998 | Tracy et al. | 510/490 |
| 5,811,384 A | * | 9/1998 | Tracy et al. | 510/424 |
| 5,846,926 A | * | 12/1998 | Tracy et al. | 510/506 |
| 5,863,886 A | | 1/1999 | Tracy et al. | |
| 5,900,397 A | * | 5/1999 | Tracy et al. | 510/421 |
| 5,914,310 A | * | 6/1999 | Li et al. | 510/499 |
| 5,922,663 A | * | 7/1999 | Gabriel et al. | 510/299 |
| 5,945,393 A | * | 8/1999 | Tracy et al. | 510/413 |
| 5,952,290 A | * | 9/1999 | Li et al. | 510/493 |
| 5,955,416 A | * | 9/1999 | Baillely et al. | 510/357 |
| 6,034,271 A | | 3/2000 | Kwetkat | |
| 6,040,288 A | * | 3/2000 | Popoff et al. | 510/466 |
| 6,121,482 A | | 9/2000 | Kwetkat et al. | |
| 6,156,721 A | * | 12/2000 | Kwetkat et al. | 510/494 |
| 6,204,297 B1 | * | 3/2001 | Tracy et al. | 516/76 |
| 6,358,914 B1 | * | 3/2002 | Gabriel et al. | 510/528 |

FOREIGN PATENT DOCUMENTS

| | | |
|---|---|---|
| DE | 4227391 | 2/1994 |
| DE | 19622612 | 10/1997 |
| DE | 19750246 | 5/1999 |
| DE | 19855080 | 9/1999 |
| EP | 0697244 | 2/1996 |
| EP | 0697245 | 2/1996 |
| EP | 0708079 | 4/1996 |
| JP | 1160430 | 6/1989 |
| JP | 1160437 | 6/1989 |
| JP | 8268865 | 10/1996 |
| JP | 8311003 | 11/1996 |
| JP | 10175934 | 6/1998 |
| WO | WO 95/19953 | 7/1995 |
| WO | WO 95/19955 | 7/1995 |
| WO | WO 96/14926 | 5/1996 |
| WO | WO 96/16930 | 6/1996 |
| WO | WO 96/25384 | 8/1996 |
| WO | WO 97/23449 | 7/1997 |
| WO | WO 97/40124 | * 10/1997 |
| WO | WO 97/46513 | 12/1997 |
| WO | WO 98/20853 | 5/1998 |

OTHER PUBLICATIONS

R. Zana, "Dimeric (Gemini) Surfactants," in *Novel Surfactants: Preparation, Application and Biodegradability*, ed. C. Holmberg, Marcel Dekker (1998), p. 241.

* cited by examiner

*Primary Examiner*—Gregory Delcotto
(74) *Attorney, Agent, or Firm*—Browning Bushman P.C.

(57) ABSTRACT

The subject invention relates to surfactant compositions of gemini surfactants and co-amphiphile(s), to a process for preparing such compositions, and to their uses, especially as emulsifiers and dispersants.

23 Claims, 1 Drawing Sheet

TENSIDE COMPOSITION CONTAINING GEMINI TENSIDES AND CO-AMPHIPHILES AND PRODUCTION AND USE THEREOF

BACKGROUND OF THE INVENTION

1. Field of the Invention

This invention relates to a surfactant composition of gemini surfactants and one or more co-amphiphile(s), to a process for preparing such composition, and to its uses, especially as emulsifiers and dispersants.

2. Description of the Prior Art

Mixtures of surfactants and co-amphiphiles and their use in emulsions or dispersions are well known. These mixtures have been designed for optimising the surfactant molecules pattern at the phase boundaries. When making emulsions, it is often intended to form liquid-crystalline, lamellar phases, which can be utilised to stabilise the emulsion.

Proportionate mixtures of special surfactants and co-amphiphiles are employed according to their applications. For those applications which require a high electrolyte content in aqueous solutions or emulsions/dispersions, ionic surfactants have up to now been considered to be largely unsuitable. In order to improve the selection of appropriate surfactants, efforts have been made to quantify or classify their polarities, thus enabling a more reliable assessment of the properties and application patterns. The HLB concept and its variations is mentioned here as an example of a simple approach.

Gemini surfactants, both as nonionic and cationic variants, have been known for more than twenty years, but it was not earlier than in the '90s that they stirred up a deeper interest. For a survey of the state of the art, see R. Zana, "Dimeric (Gemini) Surfactants" in *Novel Surfactants Preparation, Applications and Biodegradability*, C. Holmberg (ed.), Marcel Dekker (1998), p. 241.

Most of the recent publications deal with ionic gemini surfactants because these materials significantly enhance the interfacial activity, for instance expressed in terms of the critical micelle formation constant or the reduction in surface tension of water, in comparison with conventional surfactants.

At first gemini surfactants were mainly recommended for use in detergents and cleaning products.

JP-A 08/268 865 also describes the use of gemini surfactants in cosmetic preparations. In the formulations disclosed therein conventional anionic surfactants have been exchanged for anionic gemini surfactants, which are considerably less irritant to the skin, without laborious modification of the formulations.

EP-A-0 697 244 discloses amphoteric gemini surfactants, which can also be mixed with other anionic, nonionic, cationic, or amphoteric surfactants. Said surfactants are reported to be useful in detergents. The gemini surfactants (gemini amides) described in WO 95/19953 can be employed among others as components in customary cleaning preparations. In WO 95/19955 gemini polyethers have been disclosed as another class of gemini surfactants, which are useful for the same application mentioned hereinbefore. Mixtures of alkoxylated bisalkylphenol gemini surfactants and other surfactants are known from WO 97/23449.

In JP-A 11/60430 and JP-A 11/60437 the use of anionic gemini surfactants in cosmetics has been described. Reportedly, these surfactants can also be combined with other surfactants.

However, in contrast to what might be expected due to the substantial improvement in interfacial activity, no significant increase in efficiency or distinct improvement of application characteristics has been brought about by gemini surfactants as direct substitutes for conventional surfactants. The meagre advantage of such surfactant substitution cannot justify the effort of incorporating an additional building element in the basic structure.

SUMMARY OF THE INVENTION

It is an object of the present invention to provide a composition containing gemini surfactants and auxiliaries (hereinafter termed "surfactant composition"), which will allow to utilise the known benefits of gemini surfactants in special uses in the broadest possible spectrum of applications, thus opening up a commercially interesting larger field.

According to the present invention, the problem has been solved by providing surfactant compositions of at least one gemini surfactant and at least one co-amphiphile having an HLB value of less than 6, said surfactant composition containing from 1 to 70 wt % of gemini surfactant and from 99 to 30 wt % of coamphiphile, referring to the total quantity of gemini surfactant and co-amphiphile. The preferred embodiments of the invention are set out in the subordinate claims.

BRIEF DESCRIPTION OF THE DRAWING(S)

DESCRIPTION OF THE PREFERRED EMBODIMENT

Figure 1:
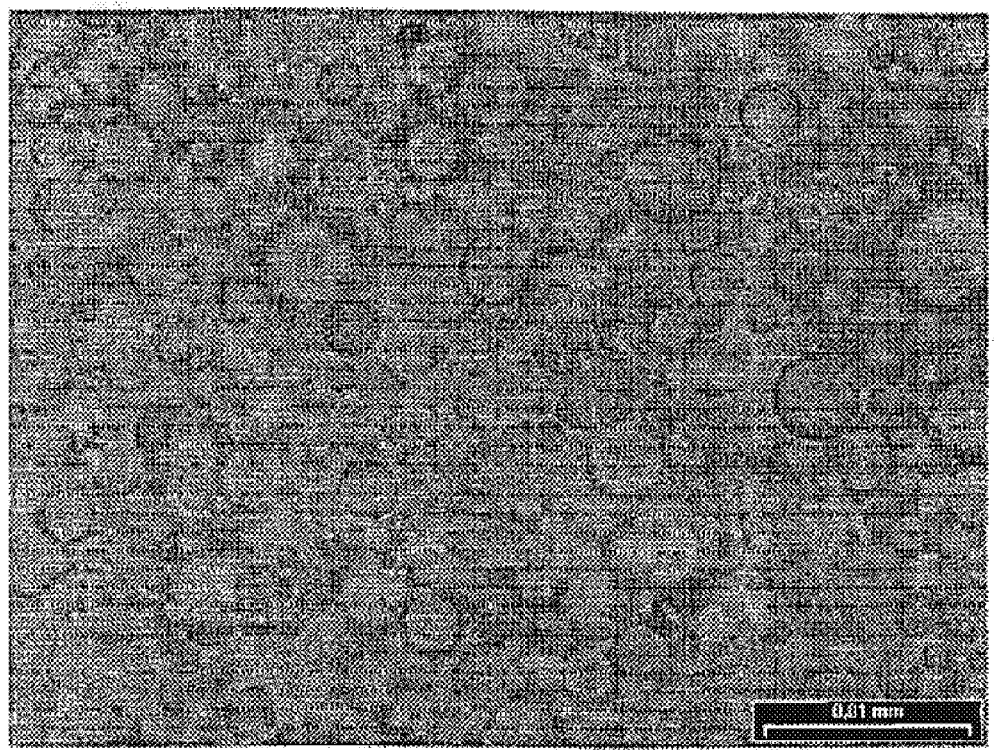
FIG. 1 depicts an O/W emulsion according to the invention prepared with Tego Care® 450 which had a viscosity of 20,000 mPas and an average droplet size in the range from 2 to 6 microns.

It has been found that the surfactant compositions of the invention containing gemini surfactants and co-amphiphiles not only optimise specific application characteristics, but also present considerable multifunctionality and greater efficiency, when compared to mixtures of conventional (non-gemini) surfactants and co-amphiphiles.

Multifunctionality is expressed for example by the surprising fact that it is possible to disperse a hydrophilic or hydrophobic pigment both in an oil phase and in a water phase (emulsifying and dispersing effect), when using the very same mixture of gemini surfactant and co-surfactant. With several of the surfactant compositions of the invention the degree of multifunctionality is even so high that one and the same surfactant composition is both an excellent emulsifier and dispersant without the need to adjust the respective emulsifier/dispersant system to the particular application. With respect to its emulsifying effect, the surfactant composition of the invention may be termed a gel network emulsifier.

The oil-in-water (O/W) emulsions prepared with the aid of the surfactant compositions of the invention are characterised by a substantially smaller oil drop size, when applying the "phase transfer temperature" method during production.

The surfactant compositions of the invention impart to the emulsions or dispersions prepared therefrom a degree of electrolyte stability which up to now has been unknown even with nonionic systems. In comparison with known complex emulsifiers, an electrolyte quantity which is greater by the factor 5 to 10 and which results in the breakdown of conventional emulsions will not produce this effect if the emulsions contain the components of the invention. The emulsions or dispersions prepared from the surfactant compositions of the invention remain stable at pH values within a range from 3 to 12.

Furthermore, the surfactant compositions of the invention have film-forming properties, which are particularly favourable regarding the large variety of applications, for example skin creams, UV protectants, or hair care products.

In addition to their technical functionality, the products are exceptionally mild. For example, by addition of the surfactant compositions of the invention to alkylether sulfates, alkylbenzene sulfonates, and other anionic surfactants the irritation potential of these substances can be distinctly reduced. The surfactant compositions are also distinguished by their high affinity for various types of interfaces. Besides the technical advantages gained when formulating different products, also application benefits have been found, such as improved combability of wet/dry hair, antistatic features, and silky touch of the skin.

This surprising multifunctionality or universal applicability has up to now been unknown both in individual surfactants and combinations of conventional surfactants and co-surfactants. It is now possible to distinctly simplify formulations, shorten formulation development work, and improve logistics. Furthermore, the application formulations thus made are much more efficient.

For the purpose of the present invention the term "gemini surfactant" is defined as a surface-active compound consisting of at least (preferably) two surfactant units, i.e., one hydrophilic head group and one hydrophobic group interlinked through at least (preferably) one spacer in proximity to the head group. Gemini surfactants are also termed dimer surfactants because of their specific structure. There exist anionic, nonionic, cationic, and amphoteric gemini surfactants, depending on the kind of head group. However, in contrast to conventional surfactants, which are grouped in the same way, gemini surfactants can also have combinations of different head groups, mostly combinations of nonionic and ionic groups.

The subject matter of the present invention relates to surfactant compositions containing anionic, cationic, and/or neutral gemini surfactants. Whenever ionic head groups are combined with nonionic ones, the ionic head group shall be predominant in the resultant gemini surfactant, such that combinations of a nonionic head group and an anionic head group can be classified as anionic gemini surfactant. The same applies to combinations of nonionic head groups with cationic or amphoteric ones.

As to the surfactant compositions of the invention, it is morphology (i.e., the relative arrangement of different structural units, namely, hydrophilic groups, spacer, hydrophobic chains) that is essential, the type of head group is not. Hence, the gemini surfactants of the present invention have the following structure:

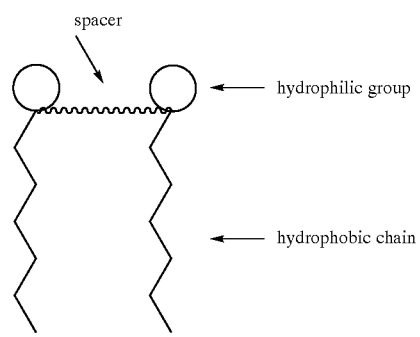

The preferred gemini surfactants used in the surfactant compositions of the invention have nitrogen atoms at the link between spacer, hydrophilic group, and hydrophobic group. More preferably, the gemini surfactants have spacers with amine or amide groups, but also spacers derived from dicarboxylic acids, betaine derived hydrophilic double head groups, optionally presenting side groups obtained by alkoxylation, especially ethoxylation, which head groups may bear sulfonic acid, phosphonic acid, carboxylic acid, or alcohol groups, including polyalcohols, each of which having hydrophobic chains with 5 to 25 carbon atoms, which are branched or unbranched and may bear up to two non-adjacent double bonds.

The following variants of gemini surfactant structures are particularly useful for the surfactant compositions of the invention.

Variant A

Structures Based on Amide- or Amine-containing Spacers

A.I Gemini Surfactants of the General Formula (A.I) According to WO 96/14926

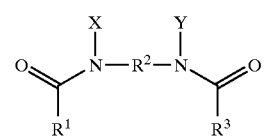

(A.I), wherein the substituents have the following meanings:

$R^1$, $R^3$ $C_5$- to $C_{25}$-alkyl, branched or unbranched, saturated, optionally unsaturated as far as not adjacently diunsaturated;

$R^2$ $C_1$- to $C_{12}$-alkylene;

X, Y $(C_2H_4O-)_x(C_3H_6O-)_y$—FR; $x+y \geq 1$, x: 0–15, y: 0–10; and

FR —$SO_3M$, —$CH_2$—$CO_2M$, —$P(O)(OM)_2$, H, —$C_3H_6SO_3M$; or —$CH_2(CHOH)_4CH_2OH$, insofar as x+y=0, wherein M=alkali, (alkyl) ammonium, alkanol ammonium, H, or ½ alkaline earth.

A.II Gemini Surfactants Having Dicarboxylic Acid-based Spacers of the General Formula (A.II) in Accordance With WO 96/25388

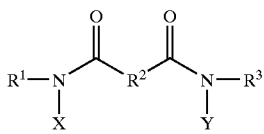

(A.II), wherein the substituents have the meanings as defined hereinabove by the general formula (A.I).

A.III Amphoteric Gemini Surfactants of the General Formula (A.III) in Accordance With WO 97/31890

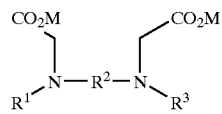

(A.III), wherein the substituents have the meanings as defined hereinabove by the general formula (A.I). Gemini surfactants of the general formula (A.III) are amphoteric compounds, which can turn into cationic ones if the ambient medium is acidic.

Variant B

Structures Based on Amide- or Amine-containing Spacers

B.I Gemini Surfactants of the General Formula (B.I) in Accordance With DE 19622612 or JP-A 10-175934

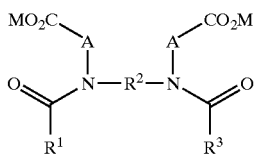

(B.I), wherein the substituents have the following meanings:
  $R^1$, $R^3$ $C_5$- to $C_{25}$-alkyl, branched or unbranched, saturated, optionally unsaturated as far as not adjacently diunsaturated;
  $R^2$ $C_1$- to $C_{12}$-alkylene;
  A $CHR^4$, $CH_2$, $C_2H_4$, $C_3H_6$, $C_4H_8$;
  $R^4$ aminocarboxylic acid radical; and
  M alkali, (alkyl) ammonium, alkanol ammonium, H, or ½ alkaline earth.

B.II Gemini Surfactants of the General Formula (B.II) in Accordance With EP 0 708 079

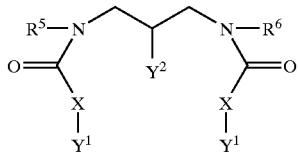

(B.II), wherein the substituents have the meanings as defined hereinabove by the general formula (B.I) and
  $R^5$, $R^6$ represent $C_6$- to $C_{36}$-alkyl, branched or unbranched, saturated, optionally unsaturated as far as not adjacently diunsaturated;
  X is an alkylene- or alkenylene group having from 1 to 6 carbon atoms, which may be substituted with a hydroxyl group or a sulfonic acid group or a carboxy group;

$Y^1$ is a sulfonate- or sulfate group or a carboxyl group, and
$Y^2$ represents a hydroxyl group, a sulfuric acid residue, or —O—(CO)X—COOH.

B.III Gemini Surfactants of the General Formula (B.III) According to JP-A-8-311003

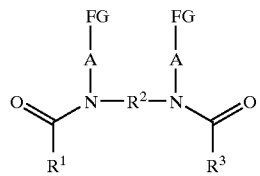

(B.III), wherein the substituents have the meanings as defined hereinabove by the general formula (B.I) and
  FG represents —COOM or —SO$_3$M.

B.IV Gemini Surfactants of the General Formula (B.IV) According to JP-A 11-60437

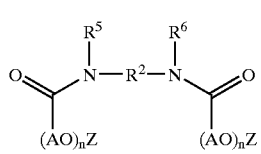

(B.IV), wherein the substituents have the meanings as defined hereinabove by the general formulas (B.I) and (B.II) and
  AO represents alkylene oxide units, i.e. ethyleneglycol-, propyleneglycol-, and butyleneglycol ether units, alone or arranged randomly or blockwise, wherein n=1 to 20, and
  Z is —SO$_3$M, —C$_2$H$_4$SO$_3$M, —C$_3$H$_6$SO$_3$M, —P(O)(OM)$_2$ or —CH$_2$—COOM, —C$_2$H$_4$—COOM.

Variant C

Structures Based on Amide- or Amine-containing Spacers

C.I Gemini Surfactants of the General Formula (C.I) According to EP 0 697 244,

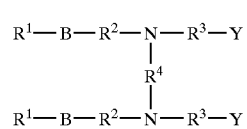

(C.I)

wherein the substituents have the following meanings:
  $R^1$ $C_5$- to $C_{25}$-alkyl, branched or unbranched, saturated, optionally unsaturated as far as not adjacently diunsaturated, hydroxy-substituted or perfluorinated;
  $R^2$ $C_1$- to $C_{12}$-alkylene or hydroxy-substituted derivatives thereof;
  B an amide group [—C(O)N(R$^2$)— or —N(R$^5$)C(O)—], a carboxyl group [—C(O)O— or —OC(O)—], a polyether group [—O(R$^6$—O)$_x$—];
  $R^5$ $C_1$- to $C_4$-alkyl or hydroxy-substituted alkyl or H;
  $R^6$ $C_2$- to $C_4$-alkylene;
  x a number from 1 to 20;
  $R^3$ $C_1$- to $C_{12}$-alkyl or hydroxy-substituted derivatives thereof, $R^7$ —D—$R^7$ or a polyether group [—O($R^6$—O)$_x$—];

$R^7$ $C_1$- to $C_6$-alkylene or hydroxy-substituted derivatives thereof;

D —O—, —S—, —N($R^8$)—;

$R^4$ alkylene or alkylaryl having from 1 to 12 carbon atoms or the hydroxy-substituted derivatives or $R^9$—D—$R^9$;

$R^8$ $C_1$- to $C_{12}$-alkyl or hydroxy-substituted alkyl or H or $R^9$—D—$R^9$;

$R^9$ $C_1$- to $C_6$-alkylene or hydroxy-substituted derivatives thereof or aryl;

$D^1$ —O—, —S—, —SO$_2$—, —C(O)—, [—O($R^7$—O)$_x$—], ($R^{10}$)$_t$[N($R^{10}$)]$_z$ or aryl;

$R^{10}$ $C_1$- to $C_{12}$-alkyl or hydroxy-substituted alkyl or H or aryl;

t, z are independently a number from 1 to 4, and

Y is independently —SO$_3$H, O—SO$_3$H, —OP(O)(OH)$_2$, —P(O)(OH)$_2$, —COOH, —CO$_2$—C$_6$H$_4$—SO$_3$H and the salts thereof.

C.II Gemini Surfactants of the General Formula (C.II) According to EP 0 697 245

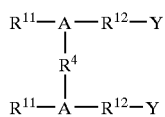

(C.II), wherein the substituents have the meanings as defined hereinabove by the general formula (C.I) and $R^{11}$ is $C_5$- to $C_{23}$-alkyl, branched or unbranched, saturated, optionally unsaturated as far as not adjacently diunsaturated, hydroxy-substituted or perfluorinated or $R^{14}$—B—$R^2$;

$R^{14}$ is $C_1$- to $C_{12}$-alkyl, branched or unbranched, saturated, optionally unsaturated as far as not adjacently diunsaturated, or the hydroxy-substituted derivatives;

$R^{12}$ means $C_1$- to $C_{12}$-alkylene, branched or unbranched, saturated, optionally unsaturated as far as not adjacently diunsaturated, or the hydroxy-substituted derivatives, or an amide group [—C(O)N($R^2$)— or —N($R^5$)C(O)—], a carboxyl group [—C(O)O— or —OC(O)—], a polyether group [—O($R^6$—O)$_x$—] or $R^9$—D—$R^9$ and A is —C$R^6$= or —N=, if whenever A is equal to —N=, $R^{11}$ represents $R^{14}$—B—$R^2$.

C.III Gemini Surfactants of the General Formula (C.III) According to DE 4227391 and DE 19608117

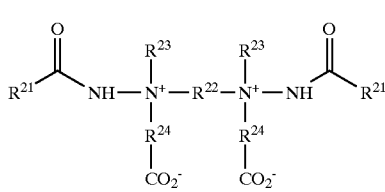

(C.III), wherein the substituents have the meanings as defined hereinabove by the general formulas (C.I) and (C.II) and $R^{21}$ represents $C_5$- to $C_{23}$-alkyl, branched or unbranched, saturated, optionally unsaturated as far as not adjacently diunsaturated;

$R^{22}$, $R^{24}$ are $C_1$- to $C_6$-alkylene;

$R^{23}$ is methyl, ethyl, propyl, or a polyether group [—O($R^6$—O)$_x$—].

Variant D

D.I Gemini Surfactants of the General Formula (D.I) According to U.S. Pat. No. 5,863,886

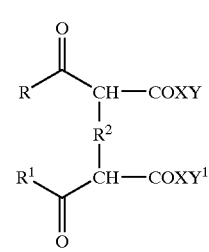

(D.I), wherein the substituents have the following meanings:

R, $R^1$ $C_5$- to $C_{30}$-alkyl, branched or unbranched, saturated, optionally unsaturated as far as not adjacently diunsaturated, hydroxy-substituted or perfluorinated;

$R^2$ $C_1$- to $C_{10}$-alkylene, arylene, and hydroxy-substituted derivatives, a polyether [—O($R^4$O)$_x$—], —S—, —SO$_2$—, —O—, —S—S—, —O—$R^5$—O—, or —S—$R^5$—S—; variable for a direct bond between the two α-carbons;

$R^4$ $C_2$- to $C_4$-alkylene;

$R^5$ $C_1$- to $C_{10}$-alkylene, arylene or alkyl arylene, —N($R^6$)—, or —(N$R^6$)—$R^7$—(N$R^6$)—;

$R^6$ $C_1$- to $C_6$-alkyl;

$R^7$ $C_1$- to $C_6$-alkyl, wherein $R^7$ and $R^6$ can also be part of a heterocyclic ring;

X polyether [—O($R^4$O)$_x$—], wherein x is a number from 1 to 30, —O—, NZ;

Z $C_1$- to $C_{10}$-alkyl, aryl, alkylaryl, or H, and

Y, $Y^1$ are independently H, —CH$_2$—COOH and salts, a hydrocarbon radical having at least two hydroxyl groups, such as erythrose, threose, ribose, arabinose, xylose, fructose, lyxose, allose, altrose, glucose, mannose, galactose and mixtures thereof.

D.II Gemini Surfactants of the General Formula (D.II)

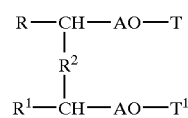

(D.II), wherein the substituents have the meanings as defined hereinabove by the general formula (D.I) and AO means —C(O)—, —C(O)—[—O($R^4$O)$_x$—], —CH$_2$—[—O($R^4$O)$_x$—], —CH$_2$—O—;

T, $T^1$ are independently —OM, —H, —CH$_3$, —C$_2$H$_5$, —SO$_3$M, —CH$_2$COOM, —C$_2$H$_4$—COOM, —C$_3$H$_6$—SO$_3$M, —O—P(O)(OM)$_2$ and M is alkyli, ½ alkaline earth, ammonium, mono-, di-, trialkanolammonium, or H.

D.III Gemini Surfactants of the General Formula (D.III) According to WO 96/16930

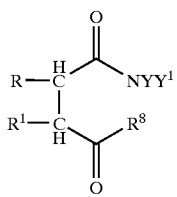

(D.III), wherein the substituents have the meanings as defined hereinabove by the general formulas (D.I) and (D.II) and
R$^8$ is NYY$^1$, —O(R$^4$O)$_x$H or —O(R$^4$O)$_x$—C(O)—CHR—CHR$^1$—C(O)NYY$^1$.

D.IV Gemini Surfactants of the General Formula (D.IV) According to WO 96/25384

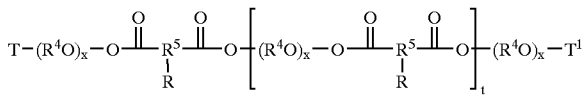

(D.IV), wherein the substituents have the meanings as defined hereinabove by the general formulas (D.I), (D.II), and (D.III) and t is an integer from 1 to 100, preferably 1 to 20, most preferably 1 to 4.

The co-amphiphiles employed according to the present invention have an HLB value of <6, calculated by the known formula HLB=E/5 (E means weight percentage of the hydrophilic moiety of the molecule).

As to the use of surfactant compositions of the present invention in emulsions, those co-amphiphiles which are solid at room temperature (25°) are particularly suitable, whereas for use in dispersions those co-amphiphiles which are liquid at room temperature are preferred. Examples of these preferable co-amphiphiles include C$_6$- to C$_{40}$-alkyl alcohols, especially C$_8$- to C$_{24}$-alkyl alcohols, most preferably cetyl alcohol or behenyl alcohol, which can be branched or unbranched, saturated or non-adjacently mono- to triunsaturated, acyclic or alicyclic, non-neutralized C$_6$- to C$_{24}$-alkylcarboxylic acids, preferably C$_8$- to C$_{22}$-alkylcarboxylic acids, which can be branched or unbranched, saturated or non-adjacently mono- to triunsaturated, acyclic or alicyclic, alkylaryl derivatives, sorbitan esters (C$_6$ to C$_{22}$), methylglucoside esters (C$_6$ to C$_{22}$), sugar esters (C$_6$ to C$_{22}$), mono-, di-, and triglycerides of C$_6$- to C$_{22}$-carboxylic acids or mixtures thereof, glycerol mono-di-stearate being particularly preferred, branched or unbranched, saturated or non-adjacently mono- to triunsaturated, mono- and di-glycerides of the aforementioned acids and their derivatives which have been further esterified with lactic acid and/or citric acid, C$_6$- to C$_{22}$-polyglycerol esters, C$_6$- to C$_{22}$-propyleneglycol esters, and also vitamin esters (e.g. vitamin E acetate, vitamin A palmitate), salicylic acid, benzoic acid, lecithins (of vegetable oils or animals). The alcohols, acids, and mono- and diglycerides of the aforementioned carboxylic acids are especially preferred.

The surfactant compositions of the invention are pre-sent as mixtures of from 1 to 70 wt %, preferably from 5 to 60 wt %, most preferably from 5 to 40 wt % of gemini surfactant or of a mixture of appropriate gemini surfactants and, accordingly, 99 to 30 wt %, preferably 95 to 40 wt %, most preferably 95 to 60 wt % of co-amphiphile. Most preferably, the surfactant compositions contain the aforementioned constituents in the quantities specified hereinabove. Within the mixing ratios of gemini surfactant(s) and co-amphiphile as specified hereinabove, it is also possible to employ mixtures of different co-amphiphiles, e.g. of up to five, preferably of three. Especially preferable mixtures are those of distinctly hydrophobic co-amphiphiles and slightly hydrophilic ones. Their proportions depend on the hydrophilicity of the gemini surfactant, i.e. if the gemini surfactant is very hydrophilic, the portion of hydrophobic co-amphiphile can be as much as 30 to 60% of the co-amphiphile quantity in the surfactant composition of the invention, with the co-amphiphiles having a difference in HLB value of greater than 2 units.

Preferable mixtures are those of long-chain alcohols (C$_6$- to C$_{40}$-alcohol, with increasing preference for C$_8$- to C$_{24}$-, C$_{14}$- to C$_{36}$-, or C$_{14}$- to C$_{24}$-alcohol), such as cetyl alcohol or behenyl alcohol, glycerol mono-di-stearate (GMS), and glycerol monostearate esterified with citric acid, or according to another embodiment of the surfactant composition of long-chain alcohols, such as cetyl alcohol or behenyl alcohol or erucic alcohol, GMS, and stearic acid, the mixtures of behenyl alcohol, GMS, and glycerol monostearate esterified with citric acid are most preferable.

Preferable surfactant compositions independently have besides the gemini surfactant, preferably in quantities of from 5 to 25 wt %, most preferably from 10 to 20 wt %, referring to the gemini surfactant/co-amphiphile(s) composition, at least two, preferably three of the different co-amphiphiles as defined hereinafter:

(a) one or more long-chain alcohol(s):
C$_6$- to C$_{40}$-alcohol, with increasing preference for C$_8$- to C$_{24}$-, C$_{14}$- to C$_{36}$-, or C$_{14}$- to C$_{24}$-al-cohol, (b) one or more long-chain acid(s):
C$_6$- to C$_{24}$-, preferably C$_8$- to C$_{22}$-carboxylic acid, (c) one or more ester(s)/partial ester(s) of a polyol with one or more mono- or polycarboxylic acid(s):
sorbitan(C$_6$- to C$_{22}$-)ester,
methylglucoside(C$_6$- to C$_{22}$-)ester,
sugar(C$_6$- to C$_{22}$-)ester,
mono-, di-, and triglyceride of a C$_6$- to C$_{22}$-carboxylic acid,
derivative (esterified with lactic acid or citric acid) of the mono- and diglycerides of C$_6$- to C$_{22}$-carboxylic acid,
polyglycerol(C$_6$- to C$_{22}$-)ester,
propyleneglycol(C$_6$- to C$_{22}$-)ester,
vitamin ester, (d) and the following additional co-amphiphiles:
salicylic acid,
benzoic acid and/or
lecithin.

According to another embodiment, the surfactant compositions of the present invention preferably have at least two, more preferably at least three of the co-amphiphiles specified hereinbelow:

(a) one or more long-chain alcohol(s) as defined hereinabove under (a) in quantities of from 30 to 50 wt %, (c1) a glycerol derivative, e.g. a mono-, di-, and triglyceride of C$_6$- to C$_{22}$-carboxylic acid, or a compound with similar HLB values, in quantities of from 30 to 50 wt %, or (b)(c2) a derivative (esterified with lactic acid or citric acid) of the mono- and diglycerides of C$_6$- to C$_{22}$- carboxylic acid and/or a $C_6$- to $C_{22}$-carboxylic acid in quantities of from 5 to 25 wt %, preferably from 10 to 20 wt %, each based on the gemini surfactant/co-amphiphiles composition.

Preferably, the long-chain alcohol is at least one of the co-amphiphiles employed herein, and an ester of a polyol with one or more mono- or polycarboxylic acid(s), preferably with 6 to 22 carbon atoms, is the other (an additional) co-amphiphile. Preferable co-amphiphiles have independently been specified hereinbelow in the patent claims.

For example, when using five co-amphiphiles, the composition of the invention preferably contains besides the gemini surfactant the following co-amphiphiles in quantities of from 5 to 25 wt %, preferably from 5 to 20 wt %:

co-amphiphile 1 long-chain alcohol as defined under (a), in quantities of from 20 to 50%, preferably from 20 to 35 wt %, co-amphiphile 2 an ester/partial ester of a polyol with one or more mono- or polycarboxylic acid(s) as defined under (c), especially GMS or a compound with a comparable HLB value, in quantities of from 20 to 50 wt %, preferably from 20 to 35 wt %, co-amphiphile 3 5 to 25%, preferably 10 to 20 wt %, co-amphiphile 4 5 to 25%, preferably 10 to 20 wt %, and co-amphiphile 5 5 to 25%, preferably 10 to 20 wt %.

According to a particularly preferable embodiment of the present invention, the composition is as follows:

| | |
|---|---|
| Gemini surfactant | 5 to 15 wt % |
| Glycerolmono-distearate | 30 to 40 wt % |
| Behenyl alcohol | 35 to 45 wt % and |
| Glycerylstearate citrate | 10 to 20 wt %. |

The gemini surfactant employed herein is most preferably a type (a) one as defined hereinabove.

Without limiting the present invention to the mechanism set forth herein, it is assumed that the surfactant compositions of the invention show a surprisingly pronounced tendency to form distinct, liquid-crystalline lamellar phases or vesicular structures with exceptional interfacial elasticity, thus allowing to prepare in a very efficient way finely dispersed, stable emulsions or very stable dispersions. The liquid-crystalline lamellar phases obtained by the aid of the surfactant compositions of the invention occupy very large spaces in the phase diagrams of the application formulations. These liquid-crystalline lamellar phases can stabilize as a gel network the respective formulations and/or can be utilized as a viscosity-imparting third phase for adjusting viscosity and spreading of the individual systems.

In O/W emulsions, i.e. in the presence of oil and water, the surfactant composition of the invention forms a third phase, depending on the mixing ratio. This third phase is a three-dimensional network, which stabilizes the separation between oil and water (water hardness is negligible when using anionic gemini surfactants) and increases the viscosity of the mixture. Hence, stabilization is further enhanced so that for example "reaming" is considerably retarded or even completely suppressed with optimal formulations. The softening point of the gel network is important for the stability of a gel network-stabilized emulsion. The softening point is heavily influenced by the melting point of the alcohol employed as a co-amphiphile. Therefore, only long-chain alcohols are employed herein.

It has been unexpectedly found with the surfactant compositions of the present invention that the very same combination can be utilized both as an extremely effec-tive emulsifier with respect to the polarity of the oil/oil mixtures employed (including silicone oil) and as a very efficient dispersant with respect to the surface of the dispersed pigment (hydrophilically or hydrophobically coated) and to the medium (dispersed in oil or water). It has so far been argued by those skilled in the art that different tasks, e.g. dispersion of a hydrophilic pigment in water or dispersion of a hydrophilic surfactant in oil, require individual solutions, i.e. individual dispersant or emulsifier combinations of gemini surfactant plus co-amphiphile(s).

It has also been surprisingly found that the surfactant compositions of the invention show very high pH- and electrolyte tolerances, thus reducing the lipid peroxide concentration, when using said mixture in a cream or lotion. Combinations with anionic surfactants have so far been considered very sensitive to electrolytes in formulations.

Process for Preparing the Aforesaid Surfactant Compositions

The phase transfer temperature method (PTT method) is a particularly preferable method of producing the surfactant compositions of the invention as emulsions with extremely small droplet size of the discontinuous phase (e.g. <1 μm). The PTT method has been modeled on the phase inversion method of producing ethoxylated surfactants (K. Shinoda, H. Saito, *J. Colloid Interface Sci.*, 34 (1969) p. 238, incorporated by reference herein) insofar as this method, too, makes use of phase transition with extremely low interfacial tension. The phase transition is characterized by transition from a micellar phase to a predominantly lamellar one. The co-amphiphile is combined shortly above the critical temperature (defined by melting point and solubility of the co-amphiphile in the oil phase) with the phase, which contains the aqueous gemini surfactant and which temperature is shortly below the critical one. When mixing the two phases, the co-amphiphile is probably absorbed to a higher degree in the micelles of the gemini surfactants. This effect is probably accelerated by the decreasing solubility in the oil phase as the temperature drops. The mixture thus obtained displays a strong tendency to form a liquid-crystalline, lamellar phase, which in fact is rapidly formed due to the rapidly growing micelles, thus resulting in surprisingly small and stable oil droplets with diameters according to this invention of preferably <1 μm.

For the production of surfactant compositions according to the present invention, this method is much more suitable than conventional emulsifying methods (see survey by J. Britto, *Euro Cosmetics*, 7–8 (1998), p.30). However, when employing the PTT method for mixtures of conventional surfactants and co-amphiphiles, their properties normally will not improve.

EXAMPLES OF APPLICATIONS

Examples of practicable applications are given below by way of illustration. The surfactant compositions of the present invention are preferably used as emulsifying or dispersing aids, as additives for conventional anionic (non-gemini) surfactants, or as additives for skin and hair cleaning formulations. The surfactant compositions of the invention are suitable for formulating O/W-, W/O-emulsions (e.g. with use of lecithin as a co-amphiphile) and microemulsions.

In addition, they are useful in cosmetics, body care and dermatological products, agrochemicals, coating materials, such as paints and lacquers (as dispersant, primer agent, additive for improving the dispersion and droplet size distribution of the organic phase in water-based lacquers), or in (printing) inks. Moreover, the emulsifying and dispersing properties of the surfactant compositions of the present invention make them appropriate for facilitating or improving pharmaceutical applications, e.g. for the controlled release of pharmaceuticals.

Hence, a special embodiment of the instant invention relates to cosmetic and dermatological preparations, such as cleaning emulsions, face and body care preparations, hair and scalp care products, mouth and teeth hygienical preparations, cosmetic and dermatological sun-screen products, and cosmetic deodorants.

The surfactant compositions of the invention are useful in the following formulations of body care, cosmetic, or dermatological preparations: pump sprays, aerosol sprays, creams, ointments, tinctures, lotions, nail care products (e.g. nail varnish, nail varnish remover, nail balm), body lotions, aftershave preparations, skin clarifiers, tanning creams, water-resistant sunscreen creams or lotions, beauty cosmetics (lip sticks, eyeliners), shampoos, antidandruffs shampoos, hair treatment products, hair conditioners, hair rinses, baby shampoos, permanent wave preparations, hair relaxer formulations (e.g. relaxer kits for removing ringlets), washing gels, shower/bathing gels and additives, handwash lotions, deodorants (e.g. rollon, stick, spray), dental care products, denture cleaners, gargles, foam baths, oil baths, oil foam baths, makeup removers, especially eye makeup removers, face cleaning creams, hair creams (pomades), moisturizing creams, skin care creams, such as daytype creams (with or without sunscreen agent), foot creams, liposome-containing gels, hair conditioning gels, depilatories (e.g. in cream form), shaving gels or foams, massage creams, cosmetic masks, foundation creams, hair-curling preparations, hair dyes, bar soap (combibar type), synthetic soaps (syndets), and liquid handwash soaps.

Examples of other components, which can be combined with the surfactant compositions of the present invention in body care or cosmetic preparations, include alkyl sarcosinates, cellulose- and guar derivatives, aromatic oils, lavender-, aniseed-, rosemary-, spruce-, and larch oil, tea-tree (*melaleuca alternifolia*) oil, or calendula oil, evening-primrose (*oenothera biennis*) oil, mouth care aromatic oils (e.g. "Dragoco ZM 0065"), perfume oils, cosmetic oils, such as avocado-, jojoba oils, or aloe vera; dialkylated acetic acid, UV absorbers (as defined by EU directive 76/768/CEE and its appendices and amendments), dihydroxyacetone, benzophenone, octyltriazone, methoxycinnamic acid and the derivatives thereof, melanine and its derivatives, long-chain dialkyl ethers, methylbenzylidene camphor, esters of salicylic acid, hyaluronic acid and its derivatives, cyclodextrines (void, e.g. as an odor inhibitor, or packed, e.g. with fragrances and/or drugs), vitamins, such as vitamin A or E, vitamin derivatives, such as vitamin A palmitate, squalane, squalene, β-carotene and other dyestuffs, tocopherol and tocopherol derivatives (e.g. tocopherol acetate), retinyl palmitate, bisabolol, dipanthenol, ascorbic acid, antioxidants, vegetable steroids (e.g. ergosterol and β-sitosterol) and their derivatives, cholesterol and its derivatives, parabenes and their derivatives (e.g. methyl-, ethyl-, propyl- and butyl parabene), pearlescent agents, anti-inflammatory agents, ceramides, pseudoceramides, imidazolidinyl urea, diiso-arachidyl dilinoleate, polymerse (e.g. polyacrylamides, carboxyvinyl polymers, maleic anhydride-oleate copolymers, polyethyleneglycol mono- or -diesters, polyvinyl-pyrrolidone, polysaccharides, polyacrylates, fluorinated hydrocarbons), cationic polymers (e.g. diethyldiallyl ammonium chloride/acrylamide copolymers, antiperspiration agents (e.g. aluminium- or circonium salts), citric acid, lactic acid, octylmethoxycinnamate, phospholipids, sodium pyrrolidone carboxylate, gelatin, alginates, albumin, collagen and its derivatives, beeswax, wax esters of long-chain carboxylic acids (branched or unbranched) and long-chain alcohols (branched or unbranched), dimethyl siloxanes (acyclic, cyclic, volatile to oily), phenyltrimethicone, xanthane rubber, starch derivatives, glycerol, ascorbic acid, polyethyleneglycols, such as their mono- and dicarboxylic acid esters, fatty acid mono-, -di-, and -triglycerides and their derivatives (-sulfates, -citrates, -lactylates, -lactates, -tartrates), carnauba wax, lecithin, chlorohexidine salts, benzethonium chloride, benzalkonium chloride, triclosane, triclocarbane, methylchloroisothiazoline, methylisothiazoline, chloroxylenol, DMDM-hydantoin, alkyltrimethylammonium-bromide, salicylic acid and its derivatives, inosite derivatives, acylated ethylenediamine derivatives, colorants approved for cosmetic applications (as defined in the publication "*Kosmetische Färbemittel*" [*Cosmetic Colorants*] by the Colorants Commission of the German Society for the Advancement of Scientific Research, Verlag Chemie, Weinheim (1984), p. 81 ff.) and alcohols of $C_6$- to $C_{24}$-, guerbet alcohols and -acids.

Further constituents are:

antioxidants, e.g. selected from the group of amino acids (e.g. glycerol, histidine, tyrosine, tryptophane) and their derivatives, imidazoles (e.g. urocanine acid) and their derivatives, peptides, such as DL-carnosine, D-carnosine, L-carnosine, and their derivatives (e.g. "Anserin X"), carotenoids, carotenes (e.g. α-carotene, β-carotene, lycopine) and their derivatives, liponic acid and its derivatives (e.g. dihydroliponic acid), aurothioglucose, and other thiols (e.g. thioredoxine, glutathione, cysteine, cystine, cyftamine and their glycosyl-, N-acetyl-, methyl-, ethyl-, propyl-, amyl-, butyl-, and lauryl-, palmitoyl-, oleyl-, linoleyl-, cholesteryl-, and glyceryl esters) and the salts thereof, dilaurylthio-dipropionate, distearylthiodipropionate, thiodipropionic acid and its derivatives (esters, ethers, peptides, lipids, nucleotides, nucleosides and salts) and sulfoximine compounds, homocysteine sulfoxiniine, buthionine-sulfones, penta-, hexa-, heptathioninesulfoxiniine) in very small compatible quantities, and also (metal-)-chelators (e.g. α-hydroxyfatty acids, palmitic acids, phytinic acids, lactoferrinic-, -hydroxy acids (e.g. citric acid, lactic acid, malic acid, humic acid, bile acid), bile extract, bilirebine, biliverdine, EDTA, and their derivatives, unsaturated fatty acids and their derivatives (e.g. γ-linolenic acid, linoleic acid, oleic acid, folic acid and their derivatives), ubiquinone and ubiquinol and their derivatives, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate) and conylcrylbenzoate of benzoic resin, rufinic acid and its derivatives, ferulic acid and its derivatives, butylhydroxytoluene, butylhydroxyanisol, nordihydroguajak uric acid, nordihydroguajaret acid, trihydroxybutyrophenone, uric acid and its derivatives, mannose and its derivatives, zinc and its derivatives (e.g. ZnO, $ZnSO_4$), selenium and its derivatives (e.g. selenium methionine), stilbenes and their derivatives (e.g. stilbene oxide, transstilbene oxide) and the derivatives (salts, esters, ethers, sugars, nucleotides, nucleosides, peptides, and lipids) of the aforementioned active agents. The antioxidants (one or more compound(s)) in the preparations are preferably used in quantities of from 0.001 to 30 wt %, more preferably from 0.05 to 20 wt %, most preferably from 1 to 10 wt %, referring to the total quantity of the preparation.

If the antioxidant(s) is (are) vitamin E and/or its derivatives, the preferable concentration is from 0.001 to 10 wt %, referring to the total quantity of the formulation. If the antioxidant(s) is (are) vitamin A or its derivatives or carotenes or their derivatives, the preferable concentration is from 0.001 to 10 wt %, referring to the total quantity of the formulation.

Further constituents are:

UVB filters (oil-soluble or water-soluble), examples of oil-soluble substances include: 3-benzylidene camphor and its derivatives, e.g. 3,4,4-trimethylbenzylidene camphor, 4-aminobenzoic acid derivatives, preferably 4-dimethylaminobenzoic acid (2-ethylhexyl)ester, 4-dimethylamino-benzoic acid-amylester, esters of cinnamic acid, preferably 4-methoxycinnamic acid(2-ethylhexyl)ester, 4-meth-oxycinnamic acid isopentyl ester; esters of salicylic acid, preferably salicylic acid (2-ethylhexyl)ester, salicylic acid(4-isopropylbenzyl) ester, salicylic acid homomenthyl ester; derivatives of benzophenone, preferably 2-hydroxy-4-methoxybenzophenone, 2-hydroxy-4-methoxy-methylbenzophenone, 2,2'-dihydroxy-4-methoxybenzo-phenone; esters of benzylmalonic acid; examples of useful water-soluble substances include 2-phenylbenzimidazole-5-sulfonic acid and its salts, e.g. sodium-, potassium-, or triethanol ammonium salts, sulfonic acid derivatives of benzophenones and their salts, sulfonic acid derivatives of 3-benzylidene camphor and their salts.

UVA filters, preferably derivatives of dibenzoyl ethane or inorganic pigments (especially ZnO), which are usually present in cosmetic and/or dermatologic preparations.

For the protection of the skin from UV rays (UVA and UVB), it is also customary to employ inorganic pigments in cosmetic preparations, such as oxides of titanium, zinc, iron, zirconium, silicon, manganese, aluminium, cerium, and mixtures thereof, and combinations (e.g. Ti- and Fe oxides), wherein the oxides are the active agents. In general, the aforementioned metal oxides have a hydrophilic (e.g. glycerol) or a hydrophobic coating, e.g. alkyl silanes or metal soaps.

Furthermore, the surfactant compositions of the invention are useful as additives, e.g. emulsifiers, or application parameter additives. They can be utilized in pesticides, especially fungicides, herbicides (e.g. with active agents like glyphosates or sulfosates), insecticides, nematocides, acaricides, and growth regulators. They emulsify the active agents to form stable sprays, which allow excellent wetting of the treated objects and con trolled release of the active substances for a prolonged period.

The surfactant compositions of the invention can also be used in decoction agents for cotton (scouring), raw wool detergents, milling agents, levelling agents, melting and preparing agents, resisting agents, reviving agents, dispersions, antielectrostatic agents, detaching agents, animal skin degreasing agents, tanning auxiliaries, and dressing/currying agents.

The surfactant compositions of the invention are also useful in disinfectants, wherein they can be combined with any customary disinfecting substances, such as phenols, cresols, chlorhexidine salts, benzethonium chloride, benzalkonium chloride, triclosane, triclocarbane, methylchloroisothiazolidine, chloroxylenol, DMDM-hydantoin, and alkyl trimethyl ammonium bromide.

Moreover, the surfactant compositions of the invention can be employed as dispersants in coating materials. For example, they effectively disperse and stabilize pigments in waterdilutable paints. Examples of dispersible in organic pigments include titanium oxide, iron oxide, cerium oxide, aluminium oxide, calcium carbonate, calcium phosphate, talc powder, kaolin, barium sulfate, aluminium- and zirconium salts, zinc oxide, silicates, and alumosilicates. Examples of organic pigments include phthalocyanine green and -blue, carbon black, and graphite. The surfactant compositions of the invention can also be employed in emulsion paints, wherein they disperse pigments and polymeric binder particles, stabilize the emulsion, and improve substrate wetting, e.g. in primers. In addition, the surfactant compositions of the invention are useful as dispersants and/or stabilizers in (printing) inks.

The surfactant compositions of the invention are also suitable as dispersants in therapeutical preparations. These applications are similar to those of cosmetics (creams, ointments, lotions, etc.).

Yet another application of the surfactant compositions of the instant invention is in emulsion- or suspension polymerization, e.g. for producing (meth)acrylate-, vinylacetate-, or vinylpropionate emulsions for paints or adhesives, or (co)polymer emulsions of acrylamide, acrylic acid, acrylates, acrylonitrile, maleic anhydride, styrene and/ or butadiene, which are produced by radical-initiated polymerization, e.g. with azoisobutyronitrile as a starter.

Prior to use in any of the aforementioned applications, the surfactant compositions of the invention can also be mixed with other components. These additional components (or additives) can be admixed prior to use or insitu.

Additives can be surfactants or completely different constituents usually employed in formulations, agents, mixtures, prepartions etc. for the respective applications. These additives are specified hereinbelow. The expert knows which one is appropriate for the respective application or formulation. Examples of preferable additives include enzymes, enzyme stabilizers, bleaching systems, chelating agents, optical brighteners, and foam inhibitors.

Besides gemini surfactants, the surfactants specified hereinbelow can be additionally employed as combinations or alone in the applications of the gemini surfactants defined herein. These surfactants can be used in quantities of from 0.1 to 99.9 wt %, based on the total quantity of the different surfactants used in the formulation. The non-limiting examples of non-ionic surfactants given herein include fatty acid glycerides, fatty acid polyglycerides, fatty acid esters, alkoxylates of higher alcohols, alkoxylated fatty acid glycerides, polyoxyethyleneoxypropyleneglycol fatty acid esters, polyoxy-ethylene sorbitan fatty acid esters, polyoxyethylene-castor oil derivatives or dehydrated castor oil derivatives, polyoxyethylene lanolin derivatives, polyoxy-ethylene fatty acid amides, polyoxyethylene alkylamines, derivatives of alkanolamines, alkylaminoxides, derivatives of protein hydrolysates, hydroxy mixed ethers, alkylmono- or -polyglycosides and alkylglucamides (e.g. N-methylalkyl-glucamides).

Examples of anionic surfactants, which are suitable for the aforesaid combinations, include soaps, ethercarboxylic acids and their salts, alkylsulfonates, α-olefin sulfonates, α-sulfofatty acid derivatives (including those specified in VVO 93/25646), dicarbonates (as defined in DE-A-196 22 612), sulfonates of higher fatty acid esters, higher alcohol sulfates (primary and secondary), alcohol ether sulfates, hydroxy mixed ether sulfates, sulfates and carbonates of alkoxylated carboxylic acid alkanol amides, salts of phosphate esters, taurides, isethionates, linear alkyl benzene sulfonates, bridged alkyl benzene sulfonates, i.e. dialkylmono- or -disulfonates of diphenyl ethers, alkylarylsulfonates, sulfates of polyoxyethylene fatty acid amides and derivatives of acylaminoacids, alkylethercarboxylic acids, alkyl- and dialkylsulfosuccinates, alkenylsulfosuccinates, alkyl- or alkenylsarcosinates, and sulfated glycerol alkylethers.

Examples of cationic surfactants, which are suitable for the aforesaid combinations, include alkyltrimethylammonium salts, dialkyldimethylammonium salts, alkyldimethylbenzylammonium salts, imidazolinium derivatives, alkylpyridinium salts, quaternized fatty acid esters of alkanolamines, alkylisoquinolinium salts, benzethonium chlorides, and cationic acylaminoacid derivatives.

Examples of ampholytic and betainic surfactants, which are suitable for the aforesaid combinations, include carbobetaines, e.g. coco-acylamidopropyldimethylbetaine, acylamidopentanediethylbetaine, dimethylammoniohexanoate-acylamidopropane-(or -ethane-)dimethyl-(or-diethyl-)-betaine, each with carbon chain lengths of from 10 to 18, sulfobetaines, imidazoline derivatives, soybean oil lipids, and lecithin. The aforementioned amine-N-oxides can also be present in polymeric form, wherein a ratio of amine to amine-N-oxide of from 10:1 to 1:1,000,000 and an average molecular mass of from 500 to 1,000,000, most preferably from 5,000 to 100,000 is required.

Examples of additional components, which can be employed alone or as combinations with the surfactant compositions of the invention, include carriers, hydrotropes, process auxiliaries, dyestuffs or pigments, perfumes, solvents for liquid formulations (most preferably alcohols with 1 to 6 carbon atoms and 1 to 6 hydroxy groups), solid fillers for bar soap formulations, pearlescent agents (e.g. distearoyl glycerides), preservatives, or buffers. If higher foaming power of a formulation is desirable, e.g. when employed in body care products, $C_{10}$- to $C_{16}$-alkanol amides can be added in quantities of from 1 to 10 wt %, referring to the total formulation. Moreover, additional water-soluble magnesium salts can be added in quantities of from 0.1 to 2 wt % in order to enhance foaming and fat dissolving power. Optionally, a few of the aforementioned surfactant compositions can also be incorporated in the formulation after they have been stabilized by adsorption on hydrophobic, porous substances and sealed with another hydrophobic coat.

EXAMPLES

The following examples illustrate several embodiments of the present invention.

Preparation of Emulsions

The micropigments utilized herein are titanium dioxide coated with aluminium and glycerol ("UV Titan M 212" manufactured by Kemira, Finland) and zinc oxide coated with dimethicone (INCI nomenclature) ("Z-Cote HP 1" manufactured by Sun Smart, USA). For comparison, commercially available emulsions are employed and analyzed.

Emulsion in water: "Tioveil AQ" (manufacturer: Tioxide), approx. 40 wt % titanium dioxide dispersed in water Emulsion in oil: "Tioveil MIG" (manufacturer: Tioxide), approx. 40 wt % titanium dioxide dispersed in capric-/caprylic triglyceride (e.g., "Miglyol 812" of CONDEA Chemie GmbH)

The particle size distribution was measured by laser light scattering. The gemini surfactant mixtures of other surfactant compositions of the subject invention is showed similar characteristics. They are included in the following tables as particle wt % <1 μm.

| Gemini Surfactant (Formula) | Variant A Structure |
|---|---|
| A.A (A.I) | $R^1 = R^3 = C_{11}H_{23}/C_{13}H_{27}$, $R^2 = C_2H_4$, $X = Y = (C_2H_4O—)_x(C_3H_6O—)_ySO_3Na$, wherein $x = 14$, $y = 0$ |
| A.B (A.I) | $R^1 = R^3 = C_{11}H_{23}/C_{13}H_{27}$, $R^2 = C_2H_4$, $X = Y = (C_2H_4O—)_x(C_3H_6O—)_yH$, wherein $x = 14$, $y = 0$ |
| A.C (A.I) | $R^1 = R^3 = C_{11}H_{23}/C_{13}H_{27}$, $R^2 = C_2H_4$, $X = Y = (C_2H_4O—)_x(C_3H_6O—)_ySO_3TIPA$, wherein $x = 11$, $y = 0$; TIPA = triisopropanol ammonium |
| A.D (A.I) | $R^1 = R^3 = C_{11}H_{23}/C_{13}H_{27}$, $R^2 = C_2H_4$, $X = Y = (C_2H_4O—)_x(C_3H_6O—)_ySO_3Na$, wherein $x = 11$, $y = 0$ |
| A.E (A.I) | $R^1 = R^3 = C_{11}H_{23}/C_{13}H_{27}$, $R^2 = C_2H_4$, $X = Y = (C_2H_4O—)_x(C_3H_6O)_yCH_2CO_2Na$, wherein $x = 14$, $y = 0$ |

| Gemini Surfactant (Formula) | Variant B Structure |
|---|---|
| B.A (B.I) | $R^1 = R^3 = C_{11}H_{23}/C_{13}H_{27}$, $R^2 = C_2H_4$, $A = CH_2$, $M = Na$ |
| B.B (B.II) | $R^5 = R^6 = C_{12}H_{25}/C_{14}H_{29}$, $X = C_2H_4$, $Y^1 = CO_2Na$, $Y^2 = —O—C(O)—C_2H_4—CO_2Na$ |
| B.C (B.II) | $R^5 = R^6 = C_{12}H_{25}/C_{14}H_{29}$, $X = C_2H_4$, $Y^1 = CO_2Na$, $Y^2 = —O—C(O)—C_2H_4—CO_2Na$ |
| B.D (B.III) | $R^1 = R^3 = C_{11}H_{23}/C_{13}H_{27}$, $R^2 = C_2H_4$, $A = C_2H_4$, $FG = —SO_3Na$ |

| Gemini Surfactant (Formula) | Variant C Structure |
|---|---|
| C.A (C.I) | $R^1 = C_{11}H_{23}$, $B = C_2H_4$, $R^3 = CH_2$, $R^4 = C_2H_4$, $Y = COONa$ |
| C.B (C.I) | $R^1 = C_{14}H_{29}$, $B = C_2H_4$, $R^3 = C_2H_4$, $R^4 = C_2H_4$, $Y = COONa$ |
| C.C (C.II) | $R^{11} = C_{12}H_{25}—C(O)—C_2H_4—$, $A = N$, $R^{12} = C_2H_4$, $R^4 = C_2H_4$, $Y = OH$ |
| C.D (C.V) | $R^{21} = C_{11}H_{23}/C_{13}H_{27}$, $R^{22}$, $R^{23}$, $R^{24} = C_2H_4$ |

| Gemini Surfactant (Formula) | Variant D Structure |
|---|---|
| D.A (D.I) | $R$, $R^1 = —C_{11}H_{23}$, $R^2 = —S—$, $X = NZ$, $Z = —CH_3$, $Y$, $Y^1$ = glucosyl residue |
| D.B (D.II) | $R$, $R^1 = —C_{11}H_{23}$, $R^2$ = single bond, $AO = —C(O)—$, $T$, $T^1 = OM$, $M = Na$ |
| D.C (D.III) | $R$, $R^1 = C_{12}H_{24}$, $R^8 = NYY1$, $Y = —CH_3$, $Y^1$ = glucosyl residue |
| D.D (D.IV) | $R^5 = —C_2H_3=$, $R = C_{12}H_{24}$, $R^4 = C_2H_4$, $x = 3$, $T$, $T^1 = H$ |

Example 1

Preparation of Pigment Emulsions in Water (Batch Size: 100 g)

The gemini surfactant and the co-amphiphile were dissolved in water at 80° C. until a slightly turbid, homogeneous emulsion was obtained. After cooling of the aqueous surfactant phase to approx. 30° C., the pigment was dispersed in the aqueous phase with stirring. The emulsion then was homogenized by stirring for five minutes with an Ultra-Turrax stirrer running at max. peripheral velocity.

| Components | wt % (m/m) |
|---|---|
| Gemini surfactant | 4.25 |
| $C_8$–$C_{10}$ fatty alcohol | 0.75 |
| Water | 45.00 |
| Pigment | 50.00 |

After 24 hours at room temperature, the particle size distribution was measured.

| Pigment | Gemini Surfactant | Median/Particle Size Distribution ($\mu$m) |
|---|---|---|
| Titanium dioxide | A.A | 0.37 |
| (UV Titan M212, Kemira) | A.B | 0.33 |
|  | A.C | 0.38 |
|  | A.D | 0.37 |
|  | A.E | 0.36 |
| Zinc oxide | A.A | 0.37 |
| (Z-Cote HP 1, Sun Smart) | A.B | 0.37 |
|  | A.C | 0.38 |
|  | A.D | 0.37 |
|  | A.E | 0.39 |
| Titanium dioxide | B.A | 0.38 |
| (UV Titan M212, Kemira) | B.B | 0.33 |
|  | C.A | 0.37 |
|  | C.B | 0.36 |
|  | D.A | 0.37 |
|  | D.B | 0.34 |

Example 2

Preparation of Titanium Dioxide Emulsions in Oil (Batch Size: 100 g)

The gemini surfactant and the co-surfactant were dissolved in oil (Miglyol 812, CONDEA Chemie GmbH) at 80° C. until a slightly turbid, homogeneous emulsion was obtained. After cooling of the surfactant phase to approx. 30° C., the pigment was admixed to the oil phase with stirring. The emulsion then was homogenized by stirring for five minutes with an Ultra-Turrax stirrer running at max. peripheral velocity.

| Components | wt % (m/m) |
|---|---|
| Gemini surfactant | 6.00 |
| Co-amphiphie, cetyl alcohol | 1.00 |
| Miglyol ® 812 | 58.00 |
| UV Titan M212 | 35.00 |

After 24 hours at room temperature, the particle size distribution was measured.

| Pigment | Gemini Surfactant | Median/Particle Size Distribution ($\mu$m) |
|---|---|---|
| Titanium oxide | A.A | 0.45 |
| (UV Titan M212, Kemira) | A.B | 0.37 |
|  | A.C | 0.44 |
|  | A.D | 0.42 |
|  | A.E | 0.38 |
|  | B.A | 0.45 |
|  | B.B | 0.37 |
|  | C.A | 0.44 |
|  | C.D | 0.43 |
|  | D.A | 0.44 |
|  | D.D | 0.43 |

Example 3

Preparation of Zinc Oxide Emulsions in Oil (Batch Size: 100 g)

The gemini surfactant and the co-amphiphile were dissolved in oil (Miglyol® 812, CONDEA Chemie GmbH) at 80° C. until a slightly turbid, homogeneous emulsion was obtained. After cooling of the surfactant phase to approx. 30° C., the pigment was admixed to the oil phase with stirring. The emulsion then was homogenized by stirring for five minutes with an Ultra-Turrax stirrer running at max. peripheral velocity.

| Components | wt % (m/m) |
|---|---|
| Gemini surfactant | 4.50 |
| Co-amphiphie, cetyl alcohol | 0.80 |
| Miglyol 812 | 44.70 |
| Z-Cote HP 1 | 50.00 |

After 24 hours at room temperature, the particle size distribution was measured.

| Variant A Pigment | Gemini Surfactant | Median/Particle Size Distribution ($\mu$m) |
|---|---|---|
| Zinc oxide | A.A | 0.41 |
| (Z-Cote HP 1, Sun Smart) | A.B | 0.37 |
|  | A.C | 0.41 |
|  | A.D | 0.40 |
|  | A.E | 0.45 |
|  | B.A | 0.41 |
|  | B.D | 0.40 |
|  | C.A | 0.42 |
|  | C.B | 0.38 |
|  | D.A | 0.42 |
|  | D.B | 0.38 |

Example 4

A combination of gemini surfactant, glyceryl stearate, glyceryl stearate citrate, and fatty alcohol was employed as a complex emulsifier:

| Complex Emulsifier A.A | [wt %] | Formulation | [wt %] |
|---|---|---|---|
| Gemini surfactant A.A | 10.00 | Complex emulsifer A.A | 1.90 |
| Glycerolmono-distearate | 35.00 | Miglyol 812 | 63.10 |
| Behenyl alcohol | 40.00 | UV Titan M212 | 35.00 |
| Glyceryl stearate citrate | 15.00 | | |

Procedure

Dissolve emulsifier in oil at 80° C., allow to cool to 30° C.

Slowly admix pigment, then disperse for 15 minutes at 1,500 rpm

Analytical Results (PSA=Particle Size Analysis)

| | D-3-2/0 | Tioveil Fin |
|---|---|---|
| PSA | | |
| Median [μm] | 0.35 | 0.33 |
| <1 μm [%] | 96.5 | 92.0 |
| Median [μm] | 0.34 | 0.35 |
| <1 μm [%] | 96.4 | 91.6 |
| Rheology | | |
| Flow point [mPa] | 5,000 | not determined |
| Viscosity (at 1 s$^{-1}$) [mPas] | 31,200 | not determined |

Example 5

The following formulation allowed to disperse a hydrophobically coated zinc oxide.

| Formulation | [wt %] |
|---|---|
| Complex emulsifier A.A | 2.0 |
| Miglyol 812 | 47.70 |
| Z-Cote HP 1 | 50.00 |

Procedure

Dissolve emulsifier in oil at 80° C., allow to cool to 30° C.

Slowly admix pigment, then disperse for 15 minutes at 1,500 rpm

This system, too, proved that the complex emulsifier is an efficient dispersant in oil:

Analytical Results (PSA=Particle Size Analysis)

| | D-3-4/0 |
|---|---|
| PSA | |
| Median [μm] | 0.38 |
| <1 μm [%] | 84.0 |

-continued

| | D-3-4/0 |
|---|---|
| Median [μm] | 0.38 |
| <1 μm [%] | 86.1 |
| Rheology | |
| Flow point [mPa] | 14,100 |
| Viscosity (at 1 s$^{-1}$) [mPas] | 39,200 |

Emulsions

Example 6 (Comparative Example)

Conventional Preparation of O/W Emulsions

| Brand | Manufacturer | CTFA/INCI Nomenclature | wt % |
|---|---|---|---|
| Phase A | | | |
| Tego Care 450 | Th. Goldschmidt | Polyglyceryl-3 methyl glucose distearate | 5.00 |
| Alternative: Gemini surfactant A.F or B.C, each plus Lanette 16 | Condea Henkel | Cetyl alcohol | 4.00 1.00 |
| Miglyol 812 N | CONDEA | Caprylic/capric triglyceride | 6.00 |
| Crodamol OP | Croda | 2-Ethylhexyl palmitate | 2.00 |
| Eutanol G | Henkel | Octyldodecanol | 2.00 |
| Softisan 100 | CONDEA | Hydrogenated coco-clycerides | 3.00 |
| Phase B | | | |
| Pricerina 9091 | Unichema | Glycerol | 3.00 |
| Demin. Wasser | | Aqua | 78.50 |
| Phase C | | | |
| Phenonip | Nipa | Phenoxyethanol methylparabene, propylparabene, butylparabene | 0.50 |
| Total | | | 100.00 |

Legend:

Gemini A.F: $R^1=R^3=C_{11}H_{23}$—/$C_{13}H_{27}$-1 $R^2=C_2H_4$, $X=Y=(C_2H_4O—)_x(C_3H_6O—)_y$; $SO_3Na$, wherein x=17, y=0 (A.I)

Preparation of Emulsion by Conventional Method:

Heat phases A and B separately to 75° C.

Admix phase A to phase B at 75° C. and homogenize for 1 minute at 75° C.

Cool the emulsion to room temperature with gentle stirring

The O/W emulsion prepared with Tego Care 450 had a viscosity of 20,600 mPa s (shear rate 1 s$^{-1}$, 25° C.) and an average droplet size in the range from 2 to 6 μm.

The O/W emulsion prepared with gemini A.F and cetyl alcohol had a viscosity of <1,000 mPa s (shear rate 1 s$^{-1}$, 25° C.). The droplet size was unsatisfactory. The O/W emulsion prepared with gemini B.C and cetyl alcohol had a viscosity of only <1,300 mPa s (shear rate 1 s$^{-1}$, 25° C.).

Example 7

Preparation of O/W Emulsions according to the PTT Method of the Subject Invention

| Brand | Manufacturer | CTFA/INCI Nomenclature | wt % |
|---|---|---|---|
| Phase A | | | |
| Tego Care 450 | Th. Goldschmidt | Polyglyceryl-3 methylglucose distearate | 5.00 |
| Alternative: | | | |
| Gemini A.F or | CONDEA | | 4.00 |
| B.C | Henkel | Cetyl alcohol | 1.00 |
| plus Lanette 16 | | | |
| Miglyol 812 N | CQNDEA | Caprylic/capric triglyceride | 10.00 |
| Phase B | | | |
| Pricerina 9091 | Unichema | Glycerol | 1.50 |
| Demin. water | | Aquar | 18.50 |
| Phase C | | | |
| Pricerina 9091 | Unichema | Glycerin | 1.50 |
| Demin. water | | | 60.00 |
| Phase D | | | |
| Phenonip | Nipa | Phenoxyethanol methylparabene, propylparabene, butylparabene | 0.50 |
| Total | | | 100.00 |

Legend:

Gemini A.F $R^1 \odot R^3 = C_{11}H_{23}-/C_{13}H_{27}-1$ $R^2 = C_2H_4$, $X=Y=(C_2H_4O-)_x(C_3H_6O-)_y$ $SO_3Na$, wherein $x=17$, $y=0$ (A.I)

Preparation of the Emulsion According to the PTT Method

Phase A was heated to 60° C. Phase B was separately heated to 50° C. Phase A then was slowly admixed to phase B with considerable homogenization. Homogenization was performed for 1 minute. Phases C and D then were admixed with gentle stirring to give a homogeneous product.

The O/W emulsion prepared with Tego Care® 450 had a vis-cosity of 20,000 mPa s (shear rate 1 s$^{-1}$, 25° C.) and an average droplet size in the range from 2 to 6 μm. This emulsion is depicted in FIG. 1 (1,100 fold magnification, Normarski interference prisma, viscosity 20,00 mPas, shear rate 1 s$^{-1}$, 25° C.). The average droplet size was in the range from 2 to 6 μm.

Figure 2:
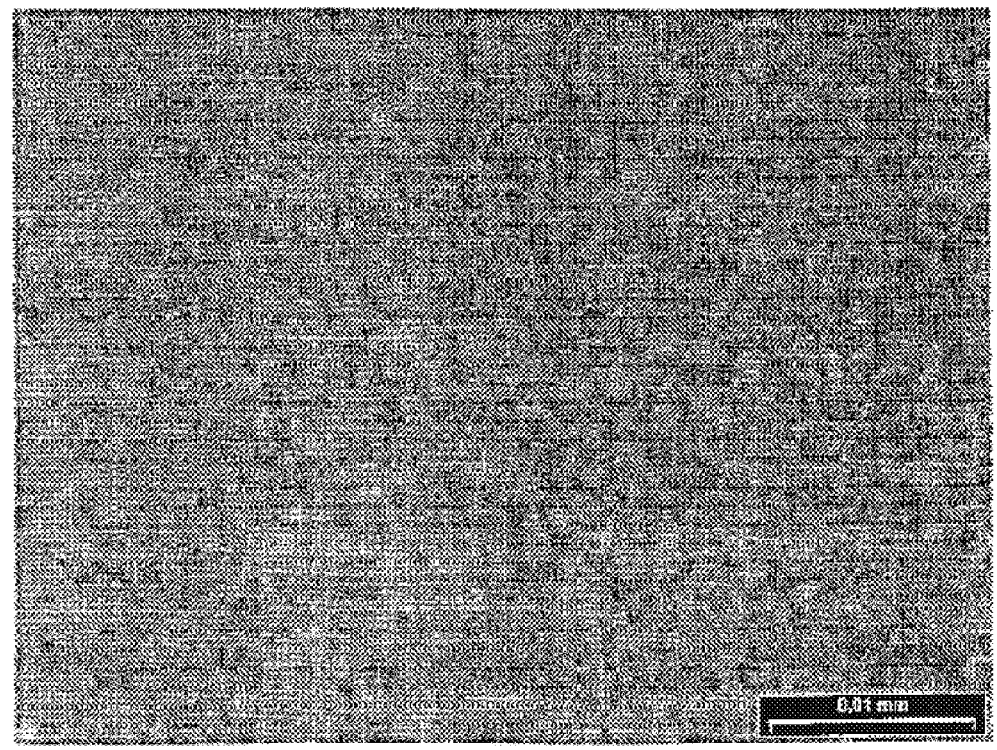
FIG. 2 depicts an O/W emulsion prepared with Gemini A.F. and cetyl alcohol. The figures demonstrate that the emulsions prepared by the PTT method using the surfactant compositions of the subject invention are distinctly superior to conventional O/W emulsions with respect to fineness and are at least equal regarding rheoeogy.

The O/W emulsion prepared with gemini A.F and cetyl alcohol is depicted in FIG. 2 (1,100 fold magnification, Normarski interference prisma, viscosity 18,000 mPas, shear rate 1 s$^{-1}$, 25° C.). The O/W emulsion prepared with gemini B.C and cetyl alcohol had a viscosity of 18,000 mPa s (shear rate 1 s$^{-1}$, 25° C.). The droplet size was <<1 μm.

The figures demonstrate that the emulsions prepared by the PTT method using the surfactant compositions of the subject invention are distinctly superior to conventional O/W emulsions with respect to fineness and are at least equal regarding rheology. Hence, when using the surfactant compositions of the invention, it is possible to produce nanoemulsions under gentle conditions and with moderate technical expenditure. Furthermore, emulsions produced with the surfactant compositions of the invention impart a silky touch.

Example 8
Test for Skin Irritation of Human Beings (Modified Duhring Chamber Test)

The formulations defined hereinbelow were prepared according to the aforementioned PTT method and were dermatologically evaluated according to the method described by Frosch and Kligman (P. J. Frosch, A. M. Kligman, The Duhring Chamber, Contact Dermatitis, 5 (1979) 73–81; P. J. Frosch, A. M. Kligman, The soap chamber test, *J. Am. Acad. Dermatol.*, 1 (1979) 35–41).

Model Formulations for the Duhring Chamber Test

| | Formulation No. | | | |
|---|---|---|---|---|
| Brand | 0-1 | 0-2 | 0-3 | 0-4 |
| Phase A | | | | |
| Tegin M | 3.00 | 3.00 | 3.00 | 3.00 |
| Gemini A.F | 1.00 | 0.00 | 0.00 | 0.00 |
| Gemini A.B | 0.00 | 0.00 | 0.00 | 1.00 |
| Emulgin B1 | 0.00 | 0.00 | 0.50 | 0.00 |
| Emulgin B2 | 0.00 | 0.00 | 0.50 | 0.00 |
| Emulgade PL1618 | 0.00 | 2.00 | 0.00 | 0.00 |
| Lanette O | 1.50 | 0.50 | 1.50 | 1.50 |
| Phase B | | | | |
| Cetiol V | 9.00 | 9.00 | 9.00 | 9.00 |
| Cetiol SN | 9.00 | 9.00 | 9.00 | 9.00 |
| Phase C | | | | |
| Water | 23.50 | 23.50 | 23.50 | 23.50 |
| Glycerol | 1.50 | 1.50 | 1.50 | 1.50 |
| Phase D | | | | |
| Water | 47.35 | 47.35 | 47.35 | 47.35 |
| Glycerol | 1.50 | 1.50 | 1.50 | 1.50 |
| Phase D | | | | |
| Keltrol | 0.15 | 0.15 | 0.15 | 0.15 |
| Phase E | | | | |
| Total | 100.00 | 100.00 | 100.00 | 100.00 |

To marked spots on the volar surface of the forearm there was applied 0.05 ml of product using aluminum chambers (Finn Chambers, 12 mm in diameter) containing adequate filter papers. The application schedule was as follows:

| | |
|---|---|
| 1st day | 18 h application–6 h pause |
| 2nd, 3rd, 4th, 5$^{th}$, and 6th day | 6 h application–18 h pause |
| 7th day | Pause |
| 8th day | Evaluation |

For comparison, water was employed as a non-irritating substance and sodium lauryl sulfate (0.2%) was chosen as an irritating agent. Three methods were employed for the evaluation: visual (in five steps), chromametry, and measurement of the transepidermal dehydration as an indicator of barrier damage. The ratings of the test substances were non-irritating, moderately irritating, fairly irritating, and strongly irritating.

Each of the four test products was found to be nonirritating, both regarding the degree of redness and the transepidermal dehydration. Statistically, no significant differences were found between the products. In contrast thereto, sodium lauryl sulfate produced the irritating effects as expected, thus confirming suitability and correct procedure of the test method.

What is claimed is:

1. A surfactant composition comprising
    (A) 1 to 70 wt %, referring to components (A) and (B), of one or more gemini surfactant(s) having the general formula (A.I):

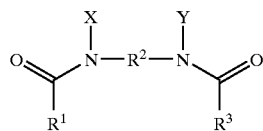

(A.I), wherein the substituents have the following meanings: $R^1$ and $R^3$ are selected from the group consisting of $C_5$ to $C_{25}$-alkyl group that can be branched, unbranched, saturated, or unsaturated as far as not adjacently diunsaturated; R2 is selected from the group consisting of $C_1$ to $C_{12}$-alkylene; X and Y are $(C_2H_4O—)_x(C_3H_6O—)_y$-FR; $x+y \geq 1$, x is from 0 to 15, y is from 0 to 10; and FR is selected from the group consisting of —$SO_3M$, —$CH_2$—$CO_2M$, —$P(O)(OM)_2$, H, —$C_3H_6SO_3M$, —$CH_2(CHOH)_4$ $CH_2OH$, insofar as x+y=0, wherein M=alkali, (alkyl) ammonium, alkanol ammonium, H or ½ alkaline earth; and, (B) referring to the remainder, based on the total of components (A) and (B), one or more co-amphiphile(s) having an HLB value of less than or equal to 6, and being selected from the group consisting of a $C_8$- to $C_{40}$-alcohol,
a methylglucoside($C_6$- to $C_{22}$-)ester,
a sugar($C_6$- to $C_{22}$-)ester,
a lactic acid- or citric acid-esterified derivative of the mono- and diglycerides of a $C_6$- to $C_{22}$-carboxylic acid,
a polyglycerol($C_6$- to $C_{22}$-)ester,
a propyleneglycol($C_6$- to $C_{22}$-)ester,
salicylic acid,
benzoic acid, and
mixtures thereof.

2. The surfactant composition of claim 1, characterized in that the surfactant composition comprises (A) 5 to 60 wt %, referring to components (A) and (B), of one or more gemini surfactant(s) and, (B) referring to the remainder, based on the total of components (A) and (B), one or more co-amphiphile (s).

3. A surfactant composition according to any of claims 1 or 2, further comprising (C) at least 0.1 wt % water, referring to the total composition.

4. A surfactant composition according to any of claims 1 or 2, further comprising (D) at least 0.1 wt % of one or more oil component(s), referring to the total composition.

5. A surfactant composition according to any of claims 1 or 2 in the form of an emulsion, characterized in that the co-amphiphile is present in solid form at 25° C.

6. A surfactant composition according to any of claims 1 or 2 in the form of a dispersion, characterized in that the co-amphiphile is present in liquid form at 25° C.

7. A surfactant composition according to any of claims 1 or 2, characterized in that at least two different co-amphiphiles are employed.

8. A surfactant composition according to any of claims 1 or 2, wherein at least one co-amphiphile is a $C_8$- to $C_{40}$-alcohol, and
mixtures thereof.

9. A surfactant composition according to claim 9, characterized in that the surfactant composition comprises 30 to 50 wt % of $C_6$ to $C_{40}$-alcohol,
30 to 50 wt %, and
mixtures thereof, each referring to the gemini surfactant/co-amphiphile(s) composition.

10. A surfactant composition according to any of claims 1 or 2 in form of an emulsion, characterized in that the surfactant composition can be produced by a method (phase transfer temperature (PTT) method), which includes at least the following step:

combining
(a) a composition (a) comprising the gemini surfactant (A) wherein the composition has a temperature X, with
(b) a composition (b) comprising the co-amphiphile (B) wherein the composition has a temperature Y, the temperature Y being greater than temperature X.

11. The surfactant composition of claim 10, characterized in that the temperature Y is not more than 15° C. higher than the critical phase transfer temperature of the surfactant in composition (b).

12. Surfactant compositions according to claim 11, characterized in that the temperatures X and Y are different by at least 3° C.

13. A surfactant composition according to any of claims 1 or 2, characterized in that the surfactant composition comprises 0.01 to 30 wt %, of the components (A) and (B), referring to the total composition.

14. The surfactant composition of claim 1 wherein said one or more gemini surfactants are present in an amount of from 10 to 60 wt %.

15. The surfactant composition of claim 2 wherein said one or more gemini surfactants are present in an amount of from 10 to 50 wt %.

16. The surfactant composition of claim 5 wherein said alcohol is a $C_8$- to $C_{24}$-alcohol.

17. The surfactant composition of claim 7 wherein 3 to 5 different co-amphiphiles are employed.

18. The surfactant composition of claim 8 wherein said alcohol is a $C_8$- to $C_{24}$-alcohol.

19. The surfactant composition of claim 9 wherein said alcohol is a $C_8$- to $C_{24}$-alcohol.

20. The surfactant composition of claim 10 wherein said composition (a) contains water.

21. The surfactant composition of claim 10 wherein said composition (b) contains an oil component.

22. The surfactant composition of claim 12 wherein the temperatures X and Y are different by at least 5°.

23. The surfactant composition of claim 13 wherein the surfactant composition comprises 0.1 to 6 wt % of the components (A) and (B), referring to the total composition.

* * * * *